(12) United States Patent
Miller et al.

(10) Patent No.: US 7,220,393 B2
(45) Date of Patent: May 22, 2007

(54) NITRIC OXIDE GAS GENERATOR

(76) Inventors: Randy Miller, Box 80, Site 1, RR2, Tofield, Alberta T0B 4J0 (CA); Christie Woodruff, 10909-69 Avenue, Edmonton, Alberta, T6H 2E4 (CA)

( * ) Notice: Subject to any disclaimer, the term of this patent is extended or adjusted under 35 U.S.C. 154(b) by 273 days.

(21) Appl. No.: 10/733,805

(22) Filed: Dec. 10, 2003

(65) Prior Publication Data

US 2004/0175309 A1    Sep. 9, 2004

(30) Foreign Application Priority Data

Dec. 10, 2002    (CA) .................................... 2413834

(51) Int. Cl.
*B01J 8/02*    (2006.01)
*B01J 7/00*    (2006.01)
*C01B 21/24*    (2006.01)

(52) U.S. Cl. ...................... 422/211; 422/198; 422/305; 423/405

(58) Field of Classification Search ................ 422/305, 422/236, 199, 239; 423/405; *C01B 21/24, C01B 21/26, 21/28, 21/30, 21/32*
See application file for complete search history.

(56) References Cited

U.S. PATENT DOCUMENTS 2,310,907 A   *   2/1943   McMillian .................. 422/191

FOREIGN PATENT DOCUMENTS

JP    61171998 A   *   8/1986

OTHER PUBLICATIONS

Ray, James D., Ogg Jr., Richard A. "A New Method of Preparing Nitric Oxide" Department of Chemistry, Stanford University, as early as Jul. 25, 1956.

* cited by examiner

*Primary Examiner*—Glenn Caldarola
*Assistant Examiner*—Jennifer A. Leung
(74) *Attorney, Agent, or Firm*—Pate Pierce & Baird

(57) ABSTRACT

A nitric oxide gas generator which includes a body having a dilution inlet chamber, a chemical mixing chamber, and a dilution outlet chamber. A dilution inlet for diluent gases is provided into the dilution inlet chamber. An inlet is provided to permit entry of the diluent gases into the chemical mixing chamber. An outlet is provided to permit the exit of diluted nitric oxide gas from the chemical mixing chamber to the dilution outlet chamber. A dilution outlet is provided for removal of diluted nitric oxide gas from the dilution outlet chamber. Supports are provided for supporting chemicals to be reacted to produce nitric oxide gas. A heat source is provided to heat the chemical mixing chamber in which chemicals are mixed to initiate a chemical reaction that produces nitric oxide gas.

2 Claims, 2 Drawing Sheets

NITRIC OXIDE GAS GENERATOR

FIELD OF THE INVENTION

The present invention relates to a nitric oxide gas generator.

BACKGROUND OF THE INVENTION

James D. Ray and Richard A. Ogg Jr. of the Department of Chemistry of Stanford University, developed and published a method of preparing nitric oxide in 1956.

SUMMARY OF THE INVENTION

What is required is a nitric oxide generator which is capable of producing nitric oxide in accordance with the teachings of the method of Ray and Ogg Jr., and diluting the pure nitric oxide into concentrations that have utility.

According to the present invention there is provided a nitric oxide gas generator which includes a body having a dilution inlet chambers, a chemical mixing chamber, and a dilution outlet chamber. A dilution inlet for diluent gases is provided into the dilution inlet chamber. An inlet is provided to permit entry of the diluent gases into the chemical mixing chamber. An outlet is provided to permit the exit of diluted nitric oxide gas from the chemical mixing chamber to the dilution outlet chamber. A dilution outlet is provided for removal of diluted nitric oxide gas from the dilution outlet chamber. Supports are provided for supporting chemicals to be reacted to produce nitric oxide gas. A heat source is provided to heat the chemical mixing chamber in which chemicals are mixed to initiate a chemical reaction that produces nitric oxide gas.

BRIEF DESCRIPTION OF THE DRAWINGS

These and other features of the invention will become more apparent from the following description in which reference is made to the appended drawings, the drawings are for the purpose of illustration only and are not intended to in any way limit the scope of the invention to the particular embodiment or embodiments shown, wherein.

DETAILED DESCRIPTION OF THE PREFERRED EMBODIMENT

Figure 1:
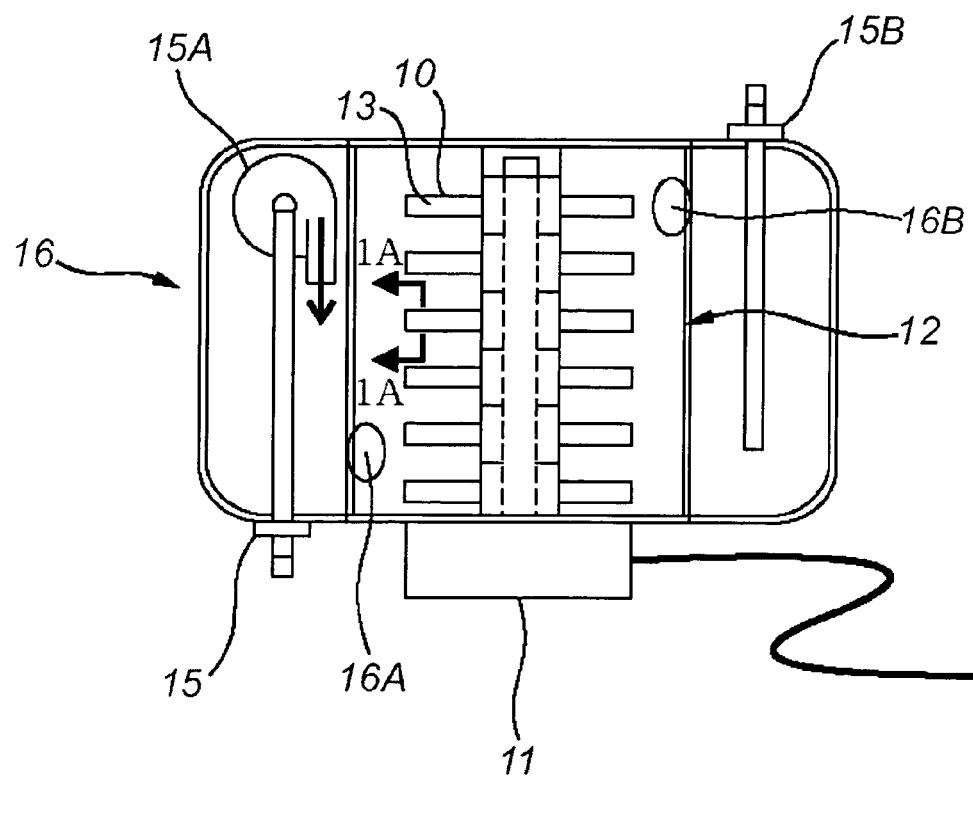
FIG. 1 is a side elevation view, in section, of a nitric oxide generator constructed in accordance with the teachings of the present invention.
Figure 1A:
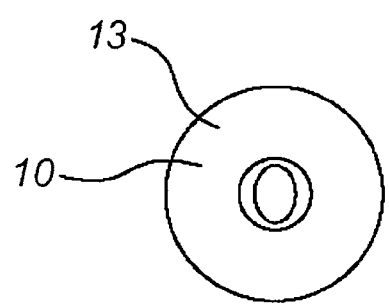
FIG. 1A is an end elevation view of chemical mixture configuration.
Figure 2:
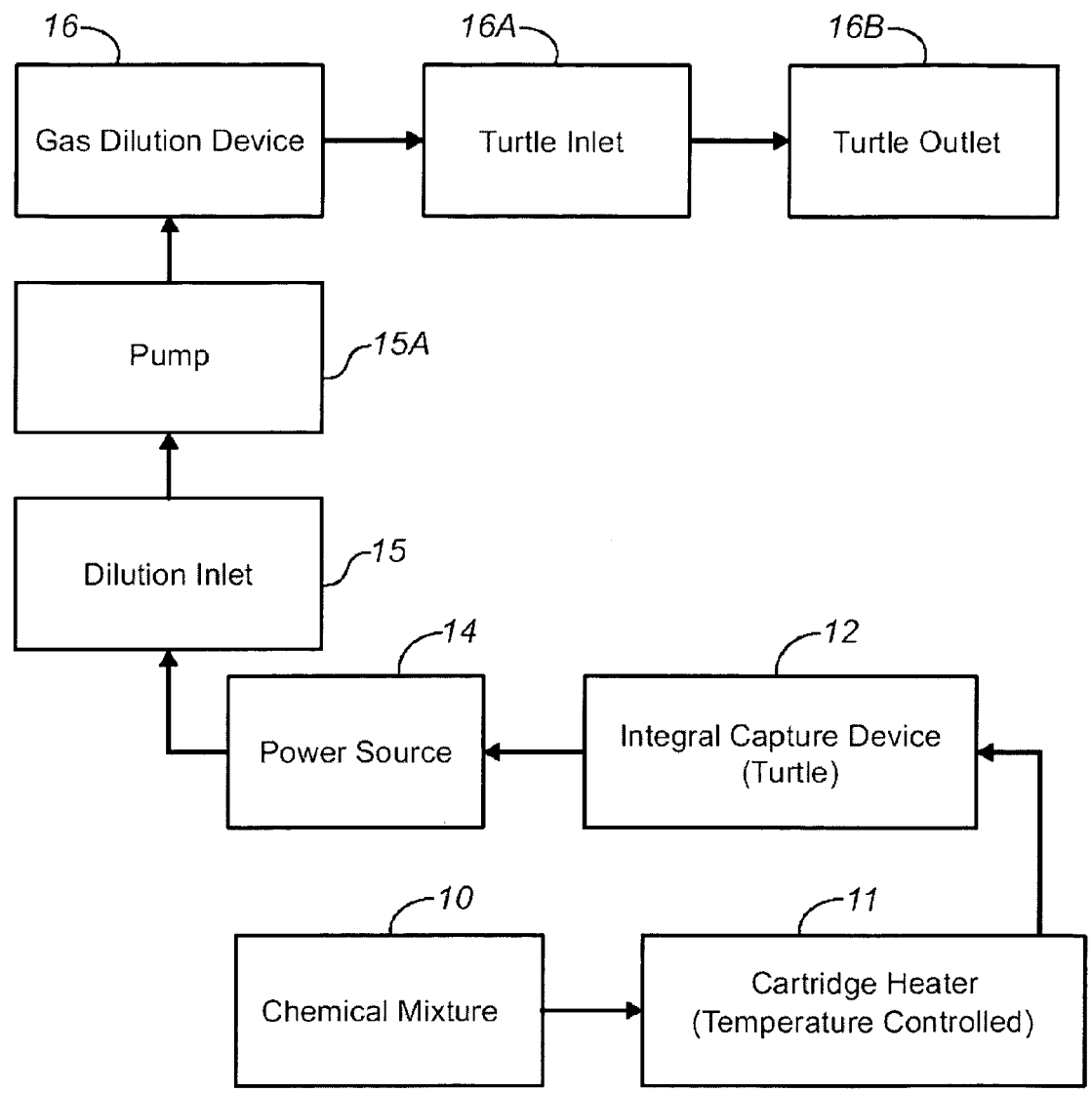
FIG. 2 is a process flow diagram which demonstrates the utility of the nitric oxide generator illustrated in FIG. 1.

The preferred embodiment, a nitric oxide gas generator will now be described with reference to FIGS. 1 and 2.

Existing Method:

(Contribution from the Department of Chemistry, Stanford University)
A New Method of Preparing Nitric Oxide
By James D. Ray and Richard A. Ogg, Jr.
Received Jul. 25, 1956

A new method of preparing nitric oxide which involves heating to a temperature slightly above 300 degrees a dry powdered mixture of potassium nitrite and nitrate, chromic oxide and ferric oxide has been perfected. The nitric oxide so produced contained only a fraction of a percent of impurity.

1. Description of Problem

One of the problems with the above method is the lack of accurate temperature control.

Solution

In order to produce reliable quantities of nitric oxide gas, the temperature must be accurately controlled. We shall do this by means of an electronically controlled electric heater and by compressing the chemical mixture into a lifesaver shape, which will allow consistent repeatable heat transfer from the heater to the mixture.

2. Description of Problem

It is necessary to capture the nitric oxide gas as it is produced and shield it from moisture, air and other unwanted contaminants.

Solution

An Integral heater and gas capture vessel (turtle shell) with appropriate fittings will resolve the problem. See FIG. 1.

3. Description of Problem

Chemical mixture inconsistency will have an adverse effect on the purity, quality, quantity and repeatability of the generated gas. Inconsistency of the generated gas is caused by settling out of the mixture components due to variations in temperature, vibration and other mechanical means.

Solution

In order to resolve inconsistencies in the chemical mixture, the chemicals will be calcined at 950 degrees Celsius in order to remove the water of hydration and then adequately mixed and compressed into a lifesaver configuration. This will prevent separation of the chemical mixture during transportation, generation of gas, shipping and handling.

4. Description of Problem

The chemical mixture will only produce pure nitric oxide (one million parts per million of nitric oxide gas is generated). What is needed is a method of varying the concentration of nitric oxide gas.

Solution

Dilution of pure nitric oxide is achieved by the entrainment of air, nitrogen, oxygen, other inert gases, or any combination thereof into the integral captured gas container. See FIG. 2.

5. Description of Problem

Impurities in the final product due to potassium nitrite not being of sufficient purity (contains about 10% potassium nitrate) are unacceptable.

Solution

Obtain commercially available potassium nitrite (potassium nitrite was not available as an article of commerce in 1956).

6. Description of Problem

The process of creating nitric oxide as described in the 1956 method of preparation is impractical for transportation.

Solution

Construct a self-contained generator (turtle). See FIG. 3.

7. Description of Problem

Control of the total Amount of Gas Produced and the Rate of Production.

Solution

Introduction of non-reactant binding reagents, configuration (lifesaver), incremental increase of reagents of known volume (size and number of lifesavers, automatic timer for heater).

8. Description of Problem

Lack of Shock Resistance, Lack of Stability of Reagents to Physical Abuse

Solution

Generator Enclosed in Turtle Shell and Lifesaver Configuration

Elements of the Nitric Oxide Gas Generator

Element 10—A Chemical Mixture

Description—The mixture is 63.75 g. (0.750 mole) potassium nitrite, 25.25 g. (0.250 mole) potassium nitrate, 76 g. (0.50 mole) chromic oxide and 120 g. (0.752 mole) ferric oxide.

Element 11—A Cartridge Heater

Description—A commercial heater capable of 310 degrees Celsius with temperature control device Element 12—Integral Gas Capture Device (Turtle)

Description—A container that captures gas created when the chemical mixture is heated.

Element 13—A Chemical Mixture Configuration

Description—A chemical mixture is compressed into a lifesaver shape that allows convenient placement of the compressed chemical onto the heater probe.

Element 14—Power Source

Description—Commercial heater powered by an electrical outlet or a rechargeable battery (depends on the volume of gas required and the portability required).

Element 15—Plumbing and Fittings Including a Dilution Inlet

Description—Commercial plumbing and fittings used as required to direct gas to the desired location.

Element 15A—Dilution Pump

Description—A pump involving positive gas flow that enhances delivery of diluent consistently Element 16—Gas Turtle a Inlet Description—This device can be a compressed nitrogen cylinder or an air entrainment device such as a pump with a calibrated orifice.

Element 16B—Turtle Inlet

Description—Allows diluent into the chemical mixing chamber (turtle)

Element 16B—Dilution Outlet

Description—Provided for the removal of diluted nitric oxide gas from the dilution outlet chamber.

Element 16B—Turtle Outlet

Description—Allows diluent to exit the chemical mixing chamber (turtle).

In this patent document, the word "comprising" is used in its non-limiting sense to mean that items following the word are included, but items not specifically mentioned are not excluded. A reference to an element by the indefinite article "a" does not exclude the possibility that more than one of the element is present, unless the context clearly requires that there be one and only one of the elements.

It will be apparent to one skilled in the art that modifications may be made to the illustrated embodiment without departing from the spirit and scope of the invention as hereinafter defined in the claims.

The embodiments of the invention in which an exclusive property or priveledge is claimed are defined as follows:

1. A nitric oxide gas generator, comprising:

a body having a dilution inlet chamber, a chemical mixing chamber, and a dilution outlet chamber, a dilution inlet for diluent gases being provided into the dilution inlet chamber, an inlet being provided to permit entry of the diluent gases from the dilution inlet chamber into the chemical mixing chamber, an outlet being provided to permit the exit of diluted nitric oxide gas from the chemical mixing chamber to the dilution outlet chamber, a dilution outlet being provided for removal of diluted nitric oxide gas from the dilution outlet chamber;

supports supporting chemicals of potassium nitrite and nitrate, chromic oxide and ferric oxide to be reacted to produce nitric oxide gas, the chemicals being powder mixed with non-reactive binders and compressed to form a compressed solid; and a heat source to heat the chemical mixing chamber in which the chemicals are mixed to initiate a chemical reaction that produces nitric oxide gas.

2. The nitric oxide generator as defined in claim 1, wherein the supports are in the form of probes extending from the heat source and the compressed solid has a lifesaver shape adapted for placement on one of the probes.

* * * * *